United States Patent
Behnke

(10) Patent No.: US 9,861,424 B2
(45) Date of Patent: Jan. 9, 2018

(54) MEASUREMENT AND CONTROL SYSTEMS AND METHODS FOR ELECTROSURGICAL PROCEDURES

(75) Inventor: Robert Behnke, Erie, CO (US)

(73) Assignee: COVIDIEN LP, Mansfield, MA (US)

(*) Notice: Subject to any disclaimer, the term of this patent is extended or adjusted under 35 U.S.C. 154(b) by 1716 days.

(21) Appl. No.: 11/827,266

(22) Filed: Jul. 11, 2007

(65) Prior Publication Data
US 2009/0018536 A1 Jan. 15, 2009

(51) Int. Cl.
| A61B 18/18 | (2006.01) |
| A61B 18/12 | (2006.01) |
| A61B 90/96 | (2016.01) |
| A61B 17/00 | (2006.01) |
| A61B 18/00 | (2006.01) |

(52) U.S. Cl.
CPC ......... *A61B 18/1206* (2013.01); *A61B 90/96* (2016.02); *A61B 2017/00725* (2013.01); *A61B 2018/00773* (2013.01); *A61B 2018/00779* (2013.01); *A61B 2018/00869* (2013.01); *A61B 2018/00988* (2013.01); *A61B 2018/1823* (2013.01)

(58) Field of Classification Search
CPC ........ A61B 18/1815; A61B 2018/1823; A61B 2018/183; A61B 2018/1838; A61B 2018/1846; A61B 2018/1853; A61B 2018/1861; A61B 2018/1869
USPC ...................................................... 606/34–38
See application file for complete search history.

(56) References Cited

U.S. PATENT DOCUMENTS

| 1,995,526 A | 3/1935 | Wappler |
| 4,204,549 A | 5/1980 | Paglione |
| 4,228,809 A | 10/1980 | Paglione |
| 4,311,154 A | 1/1982 | Sterzer et al. |
| 4,375,220 A | 3/1983 | Matvias |
| 4,446,874 A * | 5/1984 | Vaguine .................. 607/156 |

(Continued)

FOREIGN PATENT DOCUMENTS

| EP | 1 693 014 | 8/2006 |
| EP | 1707144 | 10/2006 |

(Continued)

OTHER PUBLICATIONS

European Search Report No. 11175323 dated Sep. 30, 2011.

(Continued)

*Primary Examiner* — Jaymi Della

(57) ABSTRACT

An energy delivery system for use in performing a medical procedure is provided. The medical procedure can employ an energy source, the energy source can be connected to an energy delivering device via a transmission line. The energy delivery system can include a measurement system, the measurement system can be configured to sample an output signal generated by the energy source. The energy delivery system includes a control system, which includes a calibration unit. The calibration unit can be configured to generate a calibration signal. The calibration signal can have a magnitude and phase, wherein the magnitude and phase is representative of the output signal and the transmission line loss information. The energy delivery system can also include a control unit, the control unit being configured to receive the calibration signal and adjust the energy source as needed.

7 Claims, 2 Drawing Sheets

(56) References Cited

U.S. PATENT DOCUMENTS

| | | | |
|---|---|---|---|
| 4,494,539 A | 1/1985 | Zenitani et al. | |
| 4,534,347 A * | 8/1985 | Taylor | 606/33 |
| 4,580,557 A | 4/1986 | Hertzmann | |
| 4,612,940 A | 9/1986 | Kasevich et al. | |
| 4,632,127 A | 12/1986 | Sterzer | |
| 4,632,128 A | 12/1986 | Paglione et al. | |
| 4,638,436 A | 1/1987 | Badger et al. | |
| 4,657,015 A | 4/1987 | Irnich | |
| 4,672,980 A | 6/1987 | Turner | |
| 4,741,348 A | 5/1988 | Kikuchi et al. | |
| 4,744,372 A | 5/1988 | Kikuchi et al. | |
| 4,747,416 A | 5/1988 | Kikuchi et al. | |
| 4,753,248 A | 6/1988 | Engler et al. | |
| 4,807,620 A * | 2/1989 | Strul et al. | 606/28 |
| 4,815,479 A | 3/1989 | Carr | |
| 4,860,752 A | 8/1989 | Turner | |
| 4,860,770 A | 8/1989 | Kikuchi et al. | |
| 4,873,995 A | 10/1989 | Kikuchi et al. | |
| 4,884,580 A | 12/1989 | Kikuchi et al. | |
| 4,945,912 A | 8/1990 | Langberg | |
| 4,955,377 A | 9/1990 | Lennox et al. | |
| 4,967,765 A | 11/1990 | Turner et al. | |
| 5,019,076 A | 5/1991 | Yamanashi et al. | |
| 5,025,810 A | 6/1991 | Kikuchi et al. | |
| 5,033,478 A | 7/1991 | Kikuchi et al. | |
| 5,057,106 A | 10/1991 | Kasevich et al. | |
| 5,148,814 A | 9/1992 | Kikuchi et al. | |
| 5,211,570 A | 5/1993 | Bitney | |
| 5,220,927 A | 6/1993 | Astrahan et al. | |
| 5,234,004 A | 8/1993 | Hascoet et al. | |
| 5,249,585 A | 10/1993 | Turner et al. | |
| 5,275,597 A | 1/1994 | Higgins et al. | |
| 5,295,955 A | 3/1994 | Rosen et al. | |
| 5,330,518 A * | 7/1994 | Neilson et al. | 607/101 |
| 5,342,349 A | 8/1994 | Kaufman | |
| 5,344,435 A | 9/1994 | Turner et al. | |
| 5,354,325 A | 10/1994 | Chive et al. | |
| 5,364,392 A | 11/1994 | Warner et al. | |
| 5,383,874 A | 1/1995 | Jackson et al. | |
| 5,405,346 A | 4/1995 | Grundy et al. | |
| 5,433,740 A | 7/1995 | Yamaguchi | |
| 5,445,635 A * | 8/1995 | Denen et al. | 606/27 |
| 5,571,098 A | 11/1996 | Domankevitz et al. | |
| 5,571,154 A | 11/1996 | Ren | |
| 5,584,830 A | 12/1996 | Ladd et al. | |
| 5,620,480 A | 4/1997 | Rudie | |
| 5,628,771 A | 5/1997 | Mizukawa et al. | |
| 5,693,082 A * | 12/1997 | Warner et al. | 607/156 |
| 5,800,494 A | 9/1998 | Campbell et al. | |
| 5,836,943 A | 11/1998 | Miller, III | |
| 5,904,709 A | 5/1999 | Arndt et al. | |
| 5,922,013 A | 7/1999 | Fallik | |
| 5,944,022 A | 8/1999 | Nardella et al. | |
| 5,957,969 A | 9/1999 | Warner et al. | |
| 5,961,871 A | 10/1999 | Bible et al. | |
| 5,967,976 A | 10/1999 | Larsen et al. | |
| 6,016,452 A | 1/2000 | Kasevich | |
| 6,019,757 A | 2/2000 | Scheldrup | |
| 6,022,346 A | 2/2000 | Panescu et al. | |
| 6,032,078 A | 2/2000 | Rudie | |
| 6,047,216 A | 4/2000 | Carl et al. | |
| 6,067,475 A | 5/2000 | Graves et al. | |
| 6,068,627 A | 5/2000 | Orszulak et al. | |
| 6,093,028 A | 7/2000 | Yang | |
| 6,097,985 A | 8/2000 | Kasevich et al. | |
| 6,106,520 A | 8/2000 | Laufer et al. | |
| 6,122,551 A | 9/2000 | Rudie et al. | |
| 6,134,476 A | 10/2000 | Arndt et al. | |
| 6,136,020 A | 10/2000 | Faour | |
| 6,161,048 A | 12/2000 | Sluijter et al. | |
| 6,163,726 A | 12/2000 | Wolf | |
| 6,167,313 A | 12/2000 | Gray et al. | |
| 6,175,768 B1 | 1/2001 | Arndt et al. | |
| 6,179,832 B1 | 1/2001 | Jones et al. | |
| 6,181,970 B1 | 1/2001 | Kasevich | |
| 6,188,930 B1 | 2/2001 | Carson | |
| 6,216,703 B1 | 4/2001 | Manker et al. | |
| 6,226,553 B1 | 5/2001 | Carl et al. | |
| 6,228,079 B1 | 5/2001 | Koenig | |
| 6,233,490 B1 | 5/2001 | Kasevich | |
| 6,246,912 B1 | 6/2001 | Sluijter et al. | |
| 6,251,128 B1 | 6/2001 | Knopp et al. | |
| 6,272,384 B1 | 8/2001 | Simon et al. | |
| 6,273,886 B1 | 8/2001 | Edwards et al. | |
| 6,275,738 B1 | 8/2001 | Kasevich et al. | |
| 6,289,249 B1 | 9/2001 | Arndt et al. | |
| 6,293,941 B1 | 9/2001 | Strul et al. | |
| 6,312,391 B1 | 11/2001 | Ramadhyani et al. | |
| 6,325,799 B1 | 12/2001 | Goble | |
| 6,334,074 B1 | 12/2001 | Spertell | |
| 6,347,251 B1 | 2/2002 | Deng | |
| 6,366,818 B1 | 4/2002 | Bolmsjo | |
| 6,380,815 B1 | 4/2002 | Fehrenbach et al. | |
| 6,383,183 B1 | 5/2002 | Sekino et al. | |
| 6,402,742 B1 | 6/2002 | Blewett et al. | |
| 6,430,446 B1 | 8/2002 | Knowlton | |
| 6,451,015 B1 | 9/2002 | Rittman, III et al. | |
| 6,470,217 B1 | 10/2002 | Fenn et al. | |
| 6,477,426 B1 | 11/2002 | Fenn et al. | |
| 6,485,486 B1 | 11/2002 | Trembly et al. | |
| 6,490,488 B1 | 12/2002 | Rudie et al. | |
| 6,494,880 B1 | 12/2002 | Swanson et al. | |
| 6,496,736 B1 | 12/2002 | Carl et al. | |
| 6,496,738 B2 | 12/2002 | Carr | |
| 6,503,191 B1 | 1/2003 | Miller | |
| 6,512,956 B2 | 1/2003 | Arndt et al. | |
| 6,522,931 B2 | 2/2003 | Manker et al. | |
| 6,526,320 B2 | 2/2003 | Mitchell | |
| 6,542,767 B2 | 4/2003 | McNichols et al. | |
| 6,544,069 B1 | 4/2003 | Enriquez et al. | |
| 6,582,425 B2 | 6/2003 | Simpson | |
| 6,582,427 B1 | 6/2003 | Goble et al. | |
| 6,592,579 B2 | 7/2003 | Arndt et al. | |
| 6,628,990 B1 | 9/2003 | Habib et al. | |
| 6,640,139 B1 | 10/2003 | Ueberle | |
| 6,666,862 B2 | 12/2003 | Jain et al. | |
| 6,671,535 B1 | 12/2003 | McNichols et al. | |
| 6,675,050 B2 | 1/2004 | Arndt et al. | |
| 6,685,701 B2 | 2/2004 | Orszulak et al. | |
| 6,689,131 B2 | 2/2004 | McClurken | |
| 6,690,976 B2 | 2/2004 | Fenn et al. | |
| 6,723,091 B2 | 4/2004 | Goble et al. | |
| 6,725,095 B2 | 4/2004 | Fenn et al. | |
| 6,743,225 B2 | 6/2004 | Sanchez et al. | |
| 6,752,804 B2 | 6/2004 | Simpson et al. | |
| 6,771,139 B2 | 8/2004 | Schultheiss et al. | |
| 6,788,977 B2 | 9/2004 | Fenn et al. | |
| 6,790,206 B2 | 9/2004 | Panescu | |
| 6,796,980 B2 | 9/2004 | Hall | |
| 6,823,218 B2 | 11/2004 | Berube | |
| 6,847,848 B2 | 1/2005 | Sterzer et al. | |
| 6,866,624 B2 | 3/2005 | Chornenky et al. | |
| 6,939,348 B2 | 9/2005 | Malecki et al. | |
| 6,944,504 B1 | 9/2005 | Arndt et al. | |
| 6,955,675 B2 | 10/2005 | Jain | |
| 6,957,108 B2 | 10/2005 | Turner et al. | |
| 6,962,586 B2 | 11/2005 | Berube et al. | |
| 6,974,463 B2 | 12/2005 | Magers et al. | |
| 6,986,764 B2 | 1/2006 | Davenport et al. | |
| 6,986,770 B2 | 1/2006 | Hood | |
| 6,994,704 B2 | 2/2006 | Qin et al. | |
| 7,041,096 B2 | 5/2006 | Malis et al. | |
| 7,066,933 B2 | 6/2006 | Hagg | |
| 7,089,064 B2 | 8/2006 | Manker et al. | |
| 7,093,601 B2 | 8/2006 | Manker et al. | |
| 7,105,011 B2 | 9/2006 | Auge, II | |
| 7,113,832 B2 | 9/2006 | Longo | |
| 7,115,121 B2 | 10/2006 | Novak | |
| 7,115,126 B2 | 10/2006 | Berube et al. | |
| 7,122,031 B2 | 10/2006 | Edwards et al. | |
| 7,131,445 B2 | 11/2006 | Amoah | |
| 7,169,144 B2 | 1/2007 | Hoey et al. | |
| 7,194,297 B2 | 3/2007 | Talpade et al. | |
| 7,195,627 B2 | 3/2007 | Amoah et al. | |

(56) References Cited

U.S. PATENT DOCUMENTS

| | | |
|---|---|---|
| 7,197,363 B2 | 3/2007 | Prakash et al. |
| 7,200,445 B1 | 4/2007 | Dalbee et al. |
| 7,203,556 B2 | 4/2007 | Daners |
| 7,211,081 B2 | 5/2007 | Goble |
| 7,214,224 B2 | 5/2007 | Goble |
| 7,220,260 B2 | 5/2007 | Fleming et al. |
| 7,226,447 B2 | 6/2007 | Uchida et al. |
| 2001/0008966 A1 | 7/2001 | Arndt et al. |
| 2001/0016762 A1 | 8/2001 | Carr |
| 2001/0020178 A1 | 9/2001 | Arndt et al. |
| 2002/0000234 A1 | 1/2002 | Manker et al. |
| 2002/0165529 A1 | 11/2002 | Danek |
| 2002/0193849 A1 | 12/2002 | Fenn et al. |
| 2003/0004510 A1* | 1/2003 | Wham et al. ............... 606/51 |
| 2003/0014043 A1 | 1/2003 | Henry et al. |
| 2003/0023238 A1 | 1/2003 | Manker et al. |
| 2003/0055471 A1 | 3/2003 | Fenn et al. |
| 2003/0065317 A1 | 4/2003 | Rudie et al. |
| 2003/0069619 A1 | 4/2003 | Fenn et al. |
| 2003/0144655 A1* | 7/2003 | Panescu ...................... 606/34 |
| 2003/0191513 A1 | 10/2003 | Manker et al. |
| 2003/0199863 A1 | 10/2003 | Swanson et al. |
| 2004/0032301 A1 | 2/2004 | Schultheiss et al. |
| 2004/0049254 A1 | 3/2004 | Longo |
| 2004/0106917 A1* | 6/2004 | Ormsby et al. ............ 606/33 |
| 2004/0122420 A1 | 6/2004 | Amoah |
| 2004/0133254 A1 | 7/2004 | Sterzer et al. |
| 2004/0193147 A1 | 9/2004 | Malecki et al. |
| 2004/0215179 A1 | 10/2004 | Swoyer et al. |
| 2004/0215182 A1 | 10/2004 | Lee |
| 2004/0236871 A1* | 11/2004 | Waxman ...................... 710/1 |
| 2004/0243120 A1 | 12/2004 | Orszulak et al. |
| 2004/0243200 A1 | 12/2004 | Turner et al. |
| 2005/0038419 A9 | 2/2005 | Arnold et al. |
| 2005/0137662 A1 | 6/2005 | Morris et al. |
| 2005/0143795 A1 | 6/2005 | Habib et al. |
| 2005/0149010 A1 | 7/2005 | Turovskiy et al. |
| 2005/0149012 A1 | 7/2005 | Penny et al. |
| 2005/0182393 A1 | 8/2005 | Abboud et al. |
| 2005/0228370 A1 | 10/2005 | Sterzer et al. |
| 2005/0240239 A1 | 10/2005 | Boveja et al. |
| 2005/0245920 A1 | 11/2005 | Vitullo et al. |
| 2006/0004351 A1 | 1/2006 | Arless et al. |
| 2006/0015161 A1 | 1/2006 | Longo et al. |
| 2006/0015162 A1 | 1/2006 | Edward et al. |
| 2006/0030914 A1 | 2/2006 | Eggers et al. |
| 2006/0106375 A1 | 5/2006 | Werneth et al. |
| 2006/0116673 A1 | 6/2006 | Gauthier et al. |
| 2006/0142753 A1 | 6/2006 | Francischelli et al. |
| 2006/0224152 A1* | 10/2006 | Behnke et al. ............ 606/34 |
| 2006/0287649 A1* | 12/2006 | Ormsby et al. ............ 606/33 |

FOREIGN PATENT DOCUMENTS

| | | | |
|---|---|---|---|
| JP | 2006-255405 | 9/2006 | |
| WO | 2004/047659 | * 6/2004 | ............ A61B 18/14 |

OTHER PUBLICATIONS

European Search Report for European Application No. 08012503.2 dated Sep. 19, 2008.
Canadian Office Action from Appl. No. 2,637,092 dated Jan. 23, 2015.

* cited by examiner

MEASUREMENT AND CONTROL SYSTEMS AND METHODS FOR ELECTROSURGICAL PROCEDURES

BACKGROUND

1. Technical Field

The present invention relates to systems and methods for performing a medical procedure, wherein the medical procedure includes transferring energy from an energy source to a patient via a transmission line and, more particularly, maximizing the amount of energy transferred to a patient by compensating for the losses associated with the transmission line.

2. Description of Related Art

During most medical procedures in which an energy source is employed, the energy generated for the medical procedure is transferred to a patient via a transmission line. One example of a medical procedure employing an energy source is a microwave ablation surgical procedure. In a microwave ablation surgical procedure the energy generated may be a microwave having a frequency and a wavelength associated therewith.

During the microwave ablation surgical procedure, the microwave may be transmitted to the patient via a transmission line. Generally, the transmission line employed may have losses associated therewith that may be attributable to many factors. Factors that can cause transmission line losses include at least the following: the type of material used for the transmission line, the length of the transmission line, and the thickness of the transmission line.

It is known in the art that in order to maximize the amount of energy transferred from the source (microwave generator) to the load (surgical implement), the line and load impedances should match. If the line and load impedances do not match (i.e. impedance mismatch) a reflected wave may be created, which can generate a standing wave that can contribute to the power loss associated with the impedance mismatch.

During a typical microwave ablation surgical procedure, the impedance at the surgical site changes as the microwave ablation procedure progresses. This is because of tissue necrosis associated with the microwave ablation surgical procedure. Generally, the energy source may include an impedance matching circuit and/or tuner, which may be configured to compensate for these impedance changes at the surgical site. Conventional impedance matching circuits may include devices such as capacitors and inductors. However, because the energy source is generating microwaves, which have a much smaller wavelength than the length of the transmission line, it is often difficult to obtain accurate measurements for compensation of the impedance mismatch.

SUMMARY

A measurement and control system for use in performing a medical procedure is disclosed. The medical procedure may employ an energy source, wherein the energy source may be connected to an energy delivering device via a transmission line. In one embodiment, the transmission line may be a coaxial cable.

The measurement and control system may further include a measurement system, wherein the measurement system may be configured to sample an output signal, having a magnitude and phase, that may be generated by the energy source. Additionally, the energy delivery system may include a control system, wherein the control system may include a calibration unit. The calibration unit may be configured to receive and store the loss information for the transmission line. Moreover, the calibration unit may further be configured to generate a calibration signal, wherein the calibration signal may have a magnitude and phase associated therewith. The magnitude and phase may be representative of the output signal of the measurement system and of the loss information for the transmission line.

In addition, the control system may include a control unit, wherein the control unit may be configured to receive the calibration signal and adjust the energy source in response to a value of the calibration signal.

The measurement system may be configured to include a directional coupler. The directional coupler may be configured to sample the output signal generated by the energy source.

In an embodiment, the transmission line loss information may be obtainable by storing the transmission line loss on a readable medium. In one embodiment, the readable medium may be a bar code. In an alternative embodiment, the readable medium may be a memory chip.

In another embodiment, the transmission line loss information may be obtainable via a calibration port on the energy source.

Further disclosed, is a method for measuring and controlling energy delivered to a patient from an energy source during a medical procedure. The energy source is connected to an energy delivering device via a transmission line, the method comprising the steps: a) determining losses associated with the transmission line and storing the loses in a calibration unit; b) generating an output signal from the energy source; c) sampling the output signal; d) measuring the sampled output; e) generating a calibration signal from the value of the loss information of the transmission line and the measured sampled output signal; and f) adjusting the output signal in response to the calibration signal.

In an embodiment, the step of sampling the output signal may be performed by a directional coupler.

In one embodiment, the step of determining losses associated with the transmission line may be performed by a network analyzer, wherein the loss information may be placed on the transmission line.

In yet another embodiment, the step of determining losses associated with the transmission line may be performed by a calibration port associated with the energy source.

In still yet another embodiment, the step of determining losses associated with the transmission line may be performed by a handheld device configured to perform a calibration test on the transmission line.

DETAILED DESCRIPTION

Detailed embodiments of the present disclosure are described herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
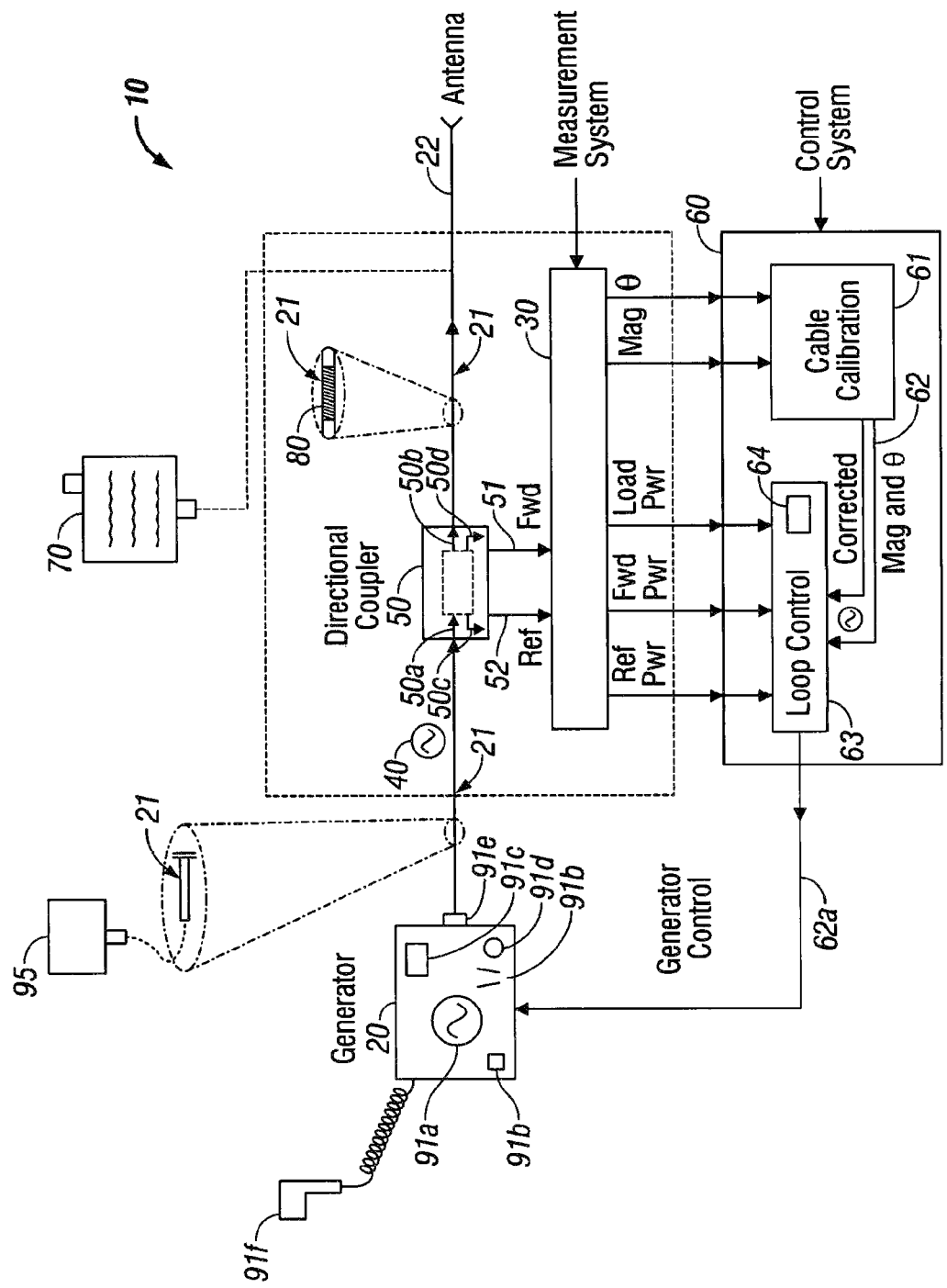
FIG. 1 is a functional block diagram of a measurement and control system according to an embodiment of the present disclosure.

Referring to FIG. 1, a measurement and control system for use in performing a medical procedure, employing an energy source in accordance with the present disclosure is generally designated 10. System 10 may be employed in an electrosurgical energy source 20 or operatively connected to an electrosurgical energy source 20. Energy source 20 may be connected to an energy delivering implement or instrument 22 (e.g., an electrosurgical pencil, a microwave ablation antenna, etc.) via a transmission line 21 (e.g., a coaxial cable) or the like.

Measurement and control system 10 includes a measurement system 30 configured to sample and measure an output signal 40 generated by energy source 20. Each output signal 40 includes a magnitude and a phase. In one embodiment, measurement system 30 includes a dual directional coupler 50, hereinafter directional coupler 50, configured to sample each output signal 40, each forward voltage and reflected voltage generated by energy source 20.

Figure 2:
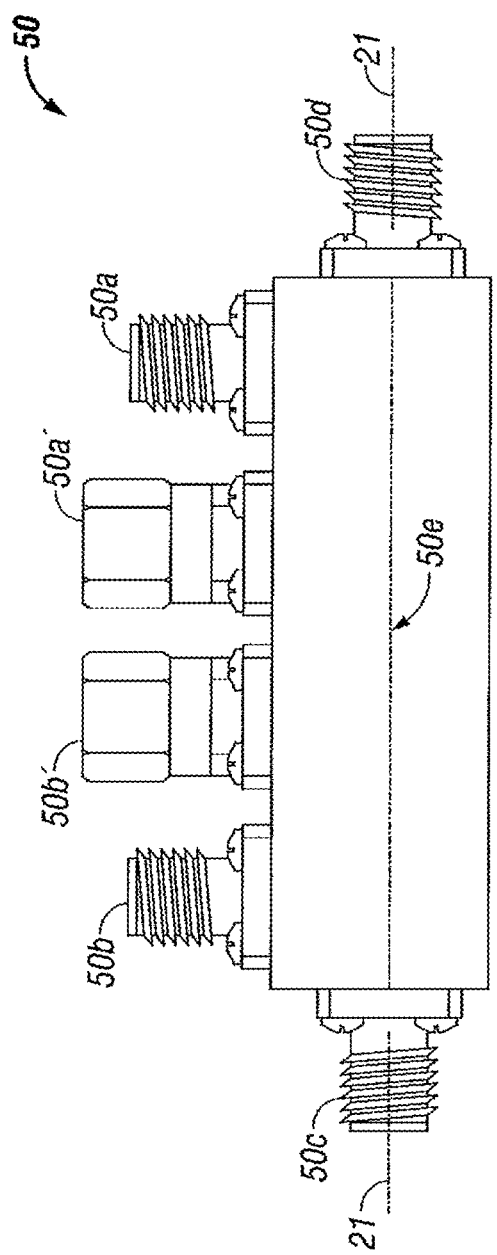
FIG. 2 is a schematic representation of a directional coupler of the measurement and control system of FIG. 1.

Directional coupler 50 may be configured to operate like most conventional dual directional couplers known in the available art. For example, as seen in FIG. 2, directional coupler 50 may sample part of the generated energy output in transmission line 21. This may be accomplished by having two transformers (not shown), which are close enough to transmission line 21 such that energy passing through transmission line 21 electrically interfaces with the two transformers. Directional coupler 50 may have two coupled ports 50a and 50b, each having an isolation port 50a' and 50b', respectively (see FIG.2). One type of dual directional coupler that may be empolyed with the present disclsoure may be the MECA 722S series manufactured by MECA ELECTRONICS, INC. In one embodiment, directional coupler 50 may have one end connected to energy source 20 via transmission line 21 and a second end connected to energy delivering implement 22, also via transmission line 21. Directional coupler 50 may also be configured to be in operative communication with measurement system 30, to be discussed in greater detail below.

In one embodiment, a main line 50e of directional coupler 50 may be designed for high power operation (large connectors), while coupled port 50c may be designed for a SubMiniature version A connector (hereinafter referrred to as "SMA"). Either isolation port 50a' or 50b' may be terminated with an internal or external matched load (typically 50 ohms). As commonly referrred to in the art, and as used in the present disclosure, the term "main line" will refer to the section between an input port 50c and transmitted port 50d.

As mentioned above and as seen in FIG. 1, directional coupler 50 may be configured to be in operative communication with measurement system 30 so that the sample output signal 40 may be directed to measurement system 30. Thus, once output signal 40 is sampled via directional coupler 50, the sampled output signal 40 may be directed to measurement system 30, wherein the sampled output signal 40 may be measured.

Measurement system 30 may be configured to measure the sampled forward and reflected voltages 51 and 52, respectively, obtained by directional coupler 50 and generated by energy source 20. The power, the magnitude and the phase of the generated output signal 40 may be obtained or calculated from the measured forward and refelected voltages 51 and 52, respectively, by conventional algorithms to be discussed in greater detail below.

Measurement and control system 10 further includes a control system 60 having a calibration unit 61 configured to receive the magnitude and the phase of the generated output signal 40 from measurement system 30 and store loss information for transmission line 21. In an embodiment, the loss information for transmission line 21 may be obtained via a network analyzer 70 and placed on a machine readable medium 80 (e.g., a bar code). In an alternative embodiment, the loss information for transmission line 21 may be obtained via a calibration port 91 located on energy source 20, as will be discussed below.

Calibration unit 61 may be further configured to generate a calibration signal 62 having a magnitude and phase associated therewith. The magnitude and phase of calibration signal 62 may be representative of each output signal 40 and the loss information for transmission line 21.

Control system 60 further includes a control unit 63 configured to receive calibration signal 62 and adjust energy source 20 as needed.

In one embodiment, the forward, reflected, and/or load power portions of sampled output signal 40 may be directed to control unit 63 and the magnitude and phase portions of the sampled output signal 40 may be directed to calibration unit 61 of control system 60, as seen in FIG. 1. Calibration unit 61 may be configured to be in operative communication with control unit 63. Control unit 63 may be opertively and selectively connected to energy source 20 and may be configured to adjust energy source 20 as needed.

As seen in FIG. 1, energy source 20 my be any suitable type of energy source including but not limited to energy sources that may be employed for performing electrosurgical procedures which may include cryosurgery, microwave ablation surgery, laser surgery, electrocautery surgery, diathermy surgery and the like. Additionally, energy source 20 may be configured to generate any suitable type of waveform. The type of waveform generated will depend on the desires and/or needs of the user, which will depend on the type of electrosurgical procedure that is being performed.

Energy source 20 may include any and all switches, buttons, knobs, ports, scanners and the likes that will allow measurement and control system 10 to function as intended.

Energy source 20 may have a scanner 91f in operative communication therewith. Scanner 91 f may be employed during calibration of transmission line 21 by network analyzer 70, wherein machine readable medium 80, placed on transmission line 21, is read by scanner 91f.

With continued reference to FIG. 1, measurement and control system 10 includes a transmission line 21 connecting antenna 22 to directional coupler 50, of control system 30. Transmission line 21 may be made from any material medium or structure that can form all or part of a path for directing the transmission of energy. Additonally, transmission line 21 may be configured to function as conventional transmission lines known in the art. That is, transmission line 21 may be configured to transfer electromagnetic waves, acoustic waves, and/or electric power transmissions.

Transmission line 21 can be in the form of a wire, coaxial cable, optical fibre, electric power line, waveguide and the like. In one embodiment, transmission line 21 is a coaxial cable configured to selectively interconnect energy delivering implement 22 and energy source 20 or control system 30.

It should be noted that the energy values or parameters (e.g., power, magnitude and phase) of output signal 40 are valid at the output of energy source 20. Thus, in order to get a more accurate reading of the energy values or parameters that are delivered to the energy delivering implement 22, one would have to know the actual losses associated with transmission line 21. Once the loss information for transmission line 21 is determined, calibration unit 61 may be used to compensate for losses of transmission line 21.

The loss information for transmission line 21 may be determined by any suitable device and/or method. For example, the loss information for transmission line 21 may be determined via network analyzer 70. In one embodiment, network analyzer 70 may be an integral part of energy source 20 or alternatively, network analyzer 70 may be a separate handheld device or member 95 that is in operative communication with energy source 20. The network analyzer 70 may be used to perform a diagnostic test of transmission line 21.

Network analyzer 70 may function in a fashion similar to most conventional network analyzers that are known in the available art. That is, network analyzer 70 may determine the properties that are associated with transmission line 21, and more particularly, those properties that are associated with transmission line 21 that affect the reflection and/or transmission of output signal 40, such as, the characteristic impedance (Zo) of transmission line 21.

Network analyzers that may be employed with measurement and control system 10 of the present disclosure may be of the type that are scalar network analyzers (hereinafter referred to as SNA), which can measure amplitude properties only. The network analyzers employed may also be of the type that are vector network analyzers (hereinafter referred to as VNA), which can measure amplitude and phase properties. Although both types of network analyzers may be employed with the present disclosure, for the remainder of the disclosure it will be assumed that the network analyzer 70 employed is a VNA.

As mentioned above, the loss information for transmission line 21 may be determined via a separate handheld device or member 95, which can be configured to perform a diagnostic test on transmission line 21. Once attached to transmission line 21, handheld device 95 may function similarly to network analyzer 70. As mentioned previously, handheld device 95 may be in operative communication with energy source 20 via an RF system and/or a port similar to port 91*d*. In operation or use, once the loss information for transmission line 21 is determined, the loss information may be sent to and/or stored in calibration unit 61.

Employing a handheld network analyzer 95 has specific utility when energy source 20 is configured without a network analyzer 70 or the like therein. For example, for loss information testing performed on transmission line 21 at times prior to its actual use, and after the manufacture process, in the event that transmission line 21 has become defective or damaged (e.g., transmission line 21 may have been bent during shipping or may have become worn because of numerous uses), a user may employ handheld network analyzer 95 to perform the loss information test on transmission line 21 immediately prior to its use. After the calibration test is completed and the loss information for transmission line 21 has been determined, the new information can then be sent to calibration unit 61.

In an alternative embodiment, energy source 20 may be configured to include a calibration port 91. In this embodiment, calibration port 91 may be operatively and selectively connected to a network analyzer 70. Network analyzer 70 may be configured to perform the necessary loss information test and send the loss information for transmission line 21 to calibration unit 61.

As mentioned previously, the loss information for transmission line 21 may also be determined as part of its manufacturing process and placed on a machine readable medium 80, and placed on transmission line 21.

Energy source 20 may include a device, in the form of a scanner or reader 91*f*, for reading a bar code and/or a memory chip. As shown in FIG. 1, reader or scanner 91*f* may be in operative communication with calibration unit 61.

The information that may be stored on the readable medium or the memory chip may be any suitable type of information that may be used to calculate the losses associated with transmission line 21, for example, the type of cable employed, the length of the cable employed, and the date that the calibration test was performed. It will be appreciated by those skilled in the art that other types of information may be stored on the readable medium or the memory chip, and as such the preceding variables should not be construed as limiting.

Following the determination of the loss information for transmission line 21 via any of the aforementioned devices and/or methods, said loss information is sent to and stored in the calibration unit 61.

As seen in FIG. 1, calibration unit 61 may be in operative communication with measurement system 30. As mentioned above, calibration unit 61 may be configured to receive and store loss information for transmission line 21 and any and all other information that is deemed necessary to a user. Calibration unit 61 may also be configured to perform any necessary calculations, via an appropriate algorithm or the like, that can correct the magnitude and phase of output signal 40 generated by energy source 20 to compensate for the loss due to transmission line 21. Calibration unit 61 may be configured to generate a calibration signal 62 relating to the magnitude and phase of output signal 40 and loss information for transmission line 21. Calibration signal 62 may be employed to correct the impedance at the energy delivering device.

Control unit 63 may be configured to receive calibration signal 62 from calibration unit 61. Control unit 63 may be configured to analyze calibration signal 62 via at least one control loop 64. In one embodiment, control loop 64 may be configured to function similarly to other conventional control loops. That is, control loop 64 may include any and all sensors, control algorithms and actuators, which may be arranged in such a fashion so as to regulate the impedance at the energy delivering implement 22.

An example of how measurement and control system 10 functions and operates now follows. It is assumed, for purposes of this example, that the loss information for transmission line 21 has been determined during the manufacture process and transmission line via bar tag 80.

Prior to use of transmission line 21, a user can scan the loss information for transmission line 21 off of bar tag 80 via any of the aforementioned methods, such as bar code scanner 91*f*. Once the loss information for transmission line 21 is scanned, the loss information may be sent to and stored in calibration unit 61, as described above.

As the electrosurgical procedure progresses, the tissue that is being treated by instrument 22 will cause the impedance at the surgical site to change, which may cause the load and line impedances to differ from one another. As used herein, "load impedance" is understood to mean the impedance actually experienced by output signal 40 and "line impedance" is understood to mean the impedance of transmission line 21. As mentioned previously, these mismatched impedances can result in the loss of electrosurgical energy between energy source 20 and instrument 22.

During the course of the electrosurgical procedure, the output signal 40 obtained and sampled by directional coupler 50, may be transmitted to calibration unit 61, wherein calibration unit 61 may perform the necessary calculations, via any number of algorithms or the like, to be discussed in greater detail below. Additionally, the phase associated with the total impedance, which includes the reactance (i.e., the imaginary part of the impedance) may be adjusted. Once the calculations are complete, calibration unit 61 may generate a calibration signal 62, which may include information regarding a magnitude and a phase for electrosurgical energy delivery. Calibration signal 62 may be directed to control unit 63 at which time control unit 63 sends the phase and magnitude information of calibration signal 62 through at least one control loop 64. After control loop 64 performs the necessary calculations, control unit 63 may adjust energy source 20 accordingly, via an output signal 62a, to compensate for the loss of transmission 21 and/or the mismatched impedances, and to deliver appropriate electrosurgical energy to instrument 22. That is, energy source 20 will transmit an output signal or electrosurgical energy which is representative of and compensates for the impedance at the surgical site and the loss information for transmission line 21.

As mentioned previously, the impedance at the surgical site increases or decreases due to tissue decomposition, a value of the impedance at the surgical site is measured and relayed or communicated to calibration unit 60. After the impedance at the surgical site is received in calibration unit 61, calibration unit 61 will generate a calibration signal 62, via any of the aforementioned devices and/or methods. Calibration signal 62 will be representative of the impedance at the surgical site and the loss information of the transmission line 21.

One can measure the impedance at the surgical site via any suitable methods known in the available art. For example, the impedance at energy source 20 may be calculated. First, the forward and reflected voltages, $V_{fwd}$ and $V_{ref}$, respectively, are measured. Then, the voltage standing wave ratio ($V_{swr}$) may be calculated using the equation:

$$V_{SWR} = \frac{V_{fwd} + V_{ref}}{V_{fwd} - V_{ref}}$$

Then, the characteristic impedance of the source ($Z_O$) and the magnitude of the load impedance ($Z_L$) may be determined using the equation:

$$\frac{Z_L - Z_O}{Z_L + Z_O} = \frac{V_{SWR} - 1}{V_{SWR} + 1}$$

Those skilled in the relative art can appreciate that the phase may easily be determined via $V_{fwd}$ and $V_{ref}$. The magnitude and the phase of $Z_L$ can then be communicated or relayed to calibration unit 60, which may be designed to adjust $Z_L$ accordingly to compensate for the losses associated with transmission line 21. After all the necessary calculations have been carried out, signal 62 of control system 60 will be an accurate representation of the actual impedance at the surgical site.

The present disclosure also provides a method for measuring and controlling energy delivered to a patient from an energy source during a medical procedure. The energy source is connected to an energy delivering device via a transmission line, the method comprising the steps: a) determining losses associated with the transmission line and storing the loses in a calibration unit; b) generating an output signal from the energy source; c) sampling the output signal; d) measuring the sampled output; e) generating a calibration signal from the value of the loss information of the transmission line and the measured sampled output signal; and f) adjusting the output signal in response to the calibration signal.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A measurement and control system for use in performing a medical procedure, comprising:
    an energy source configured to generate an output signal;
    an energy delivery instrument;
    a directional coupler;
    a transmission line including a first portion directly coupled to the energy source and the directional coupler and a second portion directly coupled to the energy delivery instrument and the directional coupler, wherein the output signal is unmodified as the output signal travels from the first portion to the second portion;
    a measurement system configured to sample the output signal generated by the energy source at the directional coupler, the sampled output signal having a magnitude and a phase, the measurement system configured to measure forward and reflected voltages of the sampled output signal to calculate forward, reflected and load power portions thereof;
    a control system including:
        a network analyzer configured to determine loss information of the transmission line;
        a calibration unit configured to receive and store the loss information for the transmission line from the network analyzer, the calibration unit further configured to receive the magnitude and phase portions of the sampled output signal and generate a calibration signal having a magnitude and a phase that are representative of the sampled output signal of the measurement system and of the loss information for the transmission line; and
        a control unit configured to receive the forward, reflected, and load power portions of the sampled output signal and the calibration signal and adjust the energy source in response to a value of the calibration signal.

2. The measurement and control system according to claim 1, wherein the transmission line is a coaxial cable.

3. The measurement and control system according to claim 1, wherein the loss information of the transmission line is stored on a readable medium.

4. The measurement and control system according to claim 3, wherein the readable medium is one of a bar code and a memory chip.

5. The measurement and control system according to claim 1, wherein the control system further includes a calibration port on the energy source configured to receive the loss information for the transmission line.

6. The measurement and control system according to claim 5, wherein the control system further includes a scanner configured to receive the loss information for the transmission line.

7. The measurement and control system according to claim 6, wherein the scanner is handheld.

\* \* \* \* \*